United States Patent [19]

Lentz

[11] Patent Number: 4,475,403
[45] Date of Patent: Oct. 9, 1984

[54] DEVICE TO PRELOAD LOADING CONNECTIONS

[75] Inventor: Thomas P. Lentz, Chanhassen, Minn.

[73] Assignee: MTS Systems Corporation, Minneapolis, Minn.

[21] Appl. No.: 389,420

[22] Filed: Jun. 17, 1982

[51] Int. Cl.³ .............................................. G01N 3/10
[52] U.S. Cl. ...................................... 73/798; 73/826; 73/856
[58] Field of Search ................ 73/796, 797, 798, 816, 73/818, 825, 826, 837, 856, 857, 859, 860; 29/446

[56] References Cited

U.S. PATENT DOCUMENTS

| | | | |
|---|---|---|---|
| 3,163,036 | 12/1964 | Lazan | 73/860 |
| 3,320,798 | 5/1967 | Gram | 73/857 |
| 3,377,847 | 4/1968 | Aske | 73/798 |
| 3,421,366 | 1/1969 | Ely | 73/93 |
| 3,563,086 | 2/1971 | Reed, Jr. | 73/92 |
| 3,800,589 | 4/1974 | Wawra et al. | 73/90 |
| 3,835,523 | 9/1974 | Stansfield | 29/452 |
| 4,018,080 | 4/1977 | Fletcher et al. | 73/15.6 |
| 4,120,230 | 10/1978 | Bunyan | 29/446 |

FOREIGN PATENT DOCUMENTS

| | | |
|---|---|---|
| 700425 | 12/1953 | United Kingdom . |
| 1220706 | 1/1971 | United Kingdom . |
| 1382192 | 1/1975 | United Kingdom . |
| 1511298 | 5/1978 | United Kingdom . |
| 1582907 | 1/1981 | United Kingdom . |

OTHER PUBLICATIONS

MTS Production Specification, Series 641 Hydraulically Operated Grips, Published by MTS Systems Corp., 1979.

Primary Examiner—Anthony V. Ciarlante
Assistant Examiner—John E. Chapman, Jr.
Attorney, Agent, or Firm—Kinney & Lange

[57] ABSTRACT

A device to permit easily preloading a grip used in specimen testing by providing load carrying links and means for stressing the links to a load level higher than that encountered during the normal loading of the grip, and providing mechanical compressive load carrying surfaces between the load applying member and the grip which are held in compression under the prestress load. Specifically, the link is formed as part of the piston rod in a hydraulic test system and a separate hydraulic chamber is subjected to pressure to load the link after which the grip can be hand threaded down into a metal surface to metal surface abutting relationship with the load applying member. Once the pressure is relieved in the auxiliary cylinder the full force of the stress in the link will hold the load applying member and the grip in contact.

14 Claims, 6 Drawing Figures

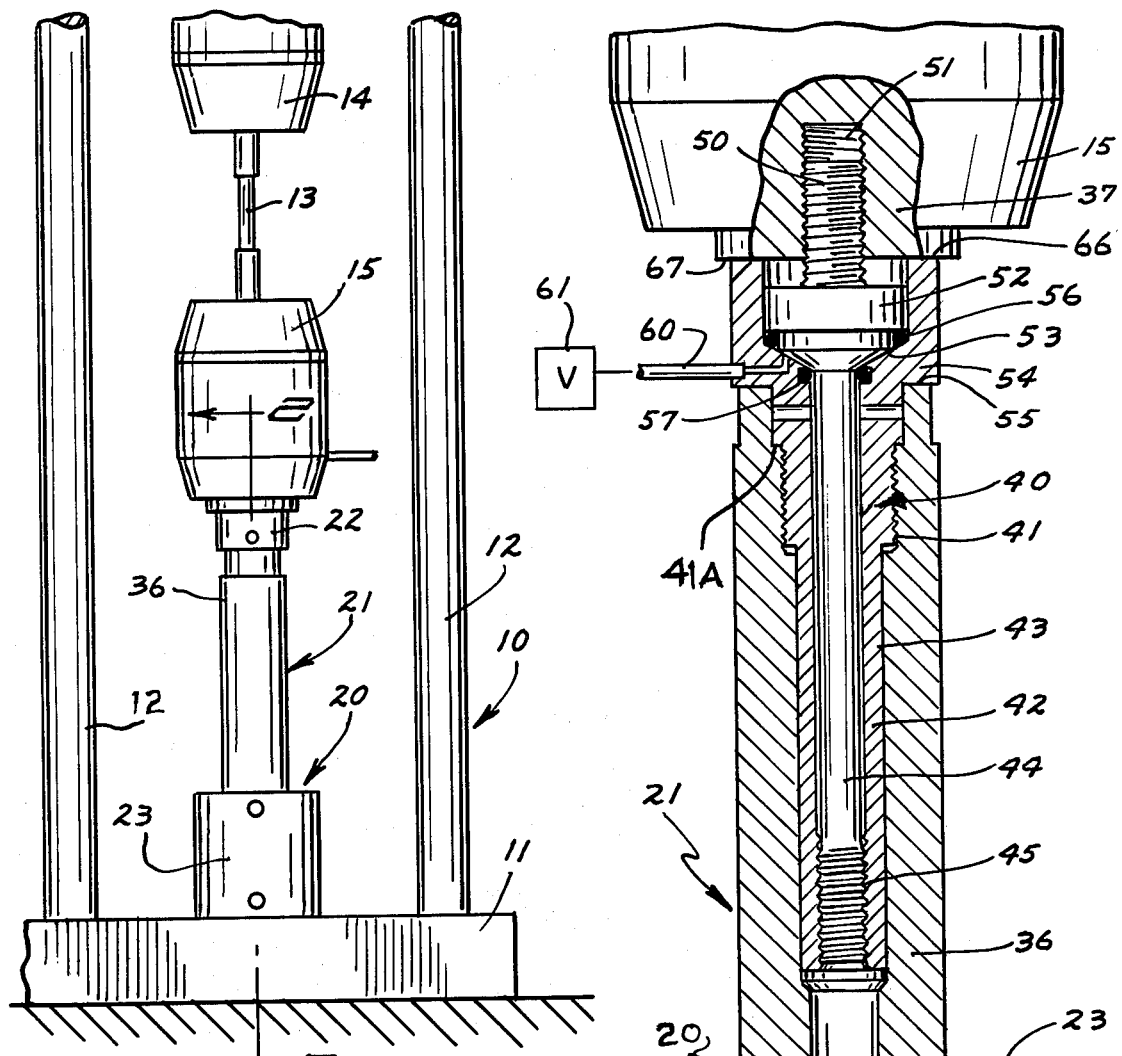
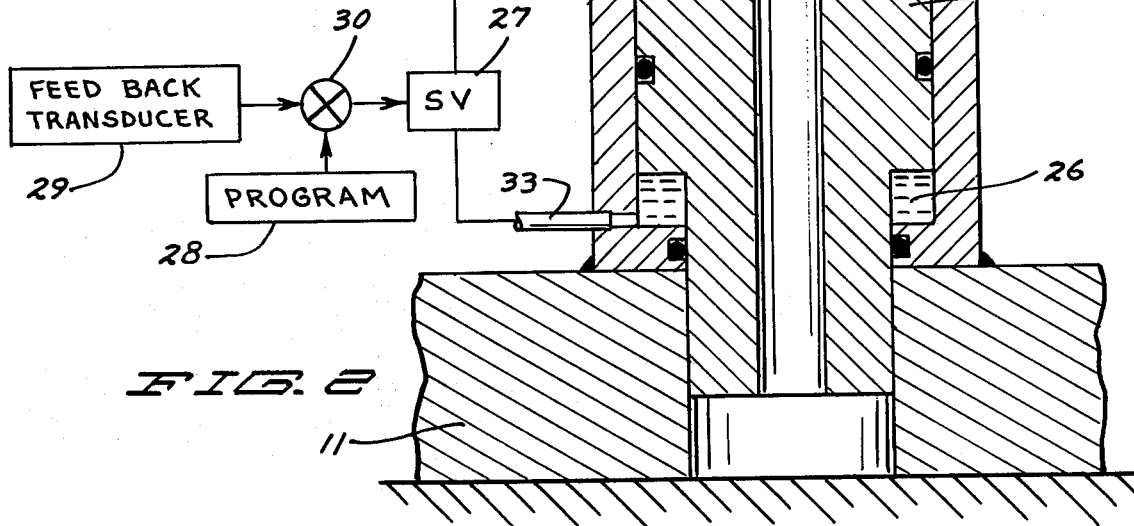
FIG. 1
FIG. 2

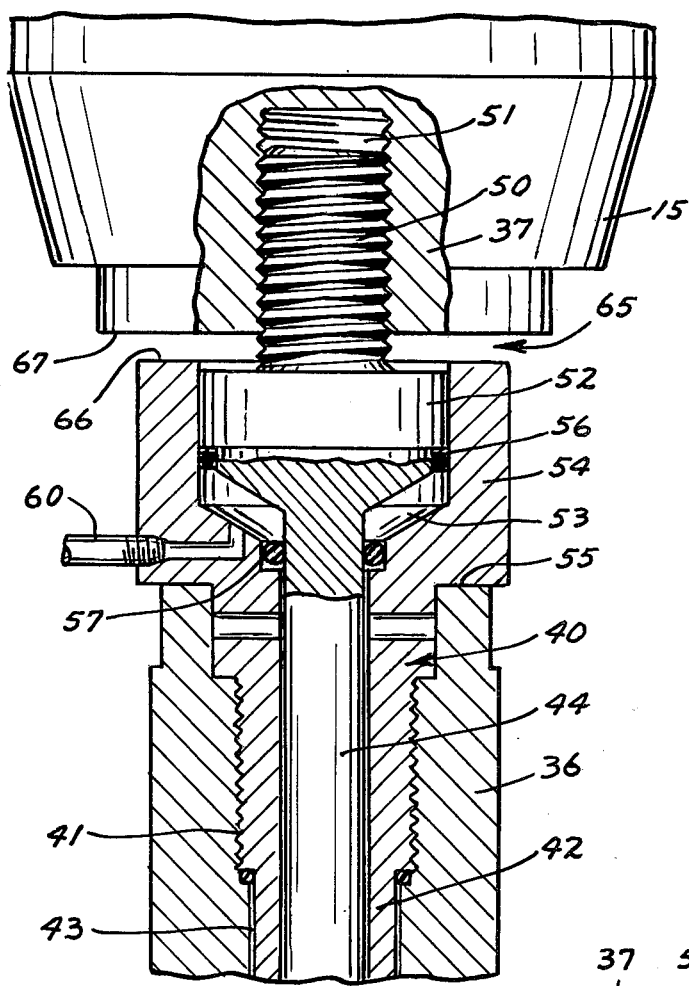
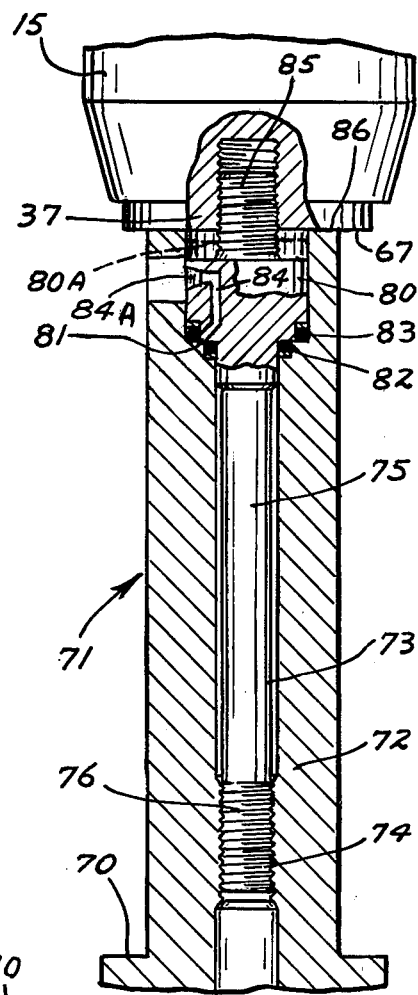
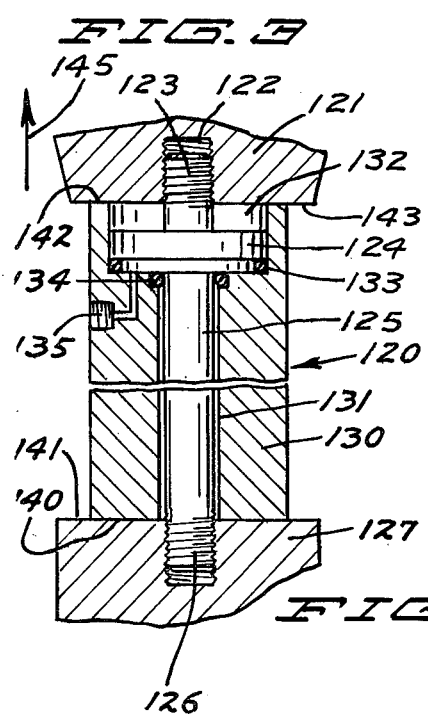
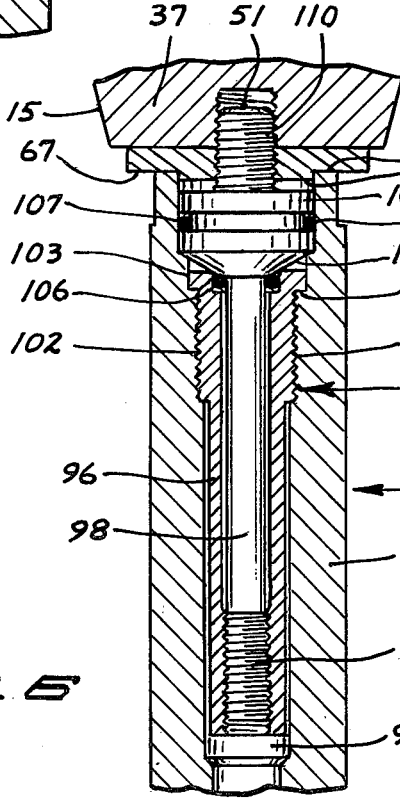
FIG.3
FIG.4
FIG.6
FIG.5

DEVICE TO PRELOAD LOADING CONNECTIONS

BACKGROUND OF THE INVENTION

1. Field of the Invention

The present invention relates to test systems, and more particularly to a device for preloading a load carrying connector that is subjected to both tension and compression forces.

2. Description of the Prior Art

In the prior art, U.S. Pat. No. 3,320,798 issued to M. M. Gram on May 23, 1967 discloses a structure for eliminating backlash in a grip used for specimen testing. In U.S. Pat. No. 3,320,798 the connecting link between the rod of an actuator and the grip is stressed by actually applying a load from the actuator through the link to increase the distance between facing shoulder surfaces on the end of the actuator rod and the end of the grip. A pair of spiral washers are then mechanically moved to increase the space between the end surfaces of this pair of washers. One of the end surfaces of the washer then contacts a surface of the grip and the other contacts the facing surface of the rod so that there is a mechanical filler between the facing surfaces of the grip and the rod.

The actuator is loaded to a tension load higher than that normally encountered during testing the specimen, so that during actual use the spiral washers remain under compression and all backlash is removed from the threaded or pinned connectors used for loading the grips.

Thus the problem of having backlash in connecting member that are loaded alternately in tension compression has long been present, and U.S. Pat. No. '798 has been effective in moving such backlash under situations where there is adequate space for the spiral washers.

Other types of tension testing machines that can utilize preloading devices or are of general interest are shown in Patents such as the following:

U.S. Pat. Nos. 3,163,036 3,421,366 3,563,086 3,800,589 4,018,080

The present device conserves space, and permits prestressing a link with a separate actuator, different from the primary testing actuator and using the stress link to eliminate backlash in the loading path.

BRIEF DESCRIPTION OF THE DRAWINGS

FIG. 1 is a fragmentary view of a typical specimen testing set up with which the preloading device of the present invention may be used;

FIG. 2 is an enlarged sectional view taken as on line 2—2 in FIG. 1;

FIG. 3 is a fragmentary enlarged view of the upper portion of the device of FIG. 2 showing details of the preloading device;

FIG. 4 is a fragmentary sectional view of an actuator rod showing a first modified form of the invention;

FIG. 5 is a vertical sectional view of a portion of an actuator rod used with a testing device and showing a further modified form of the invention; and FIG. 6 is a still further modified form of the invention showing a further modification of the invention wherein the preloading device is a separate unit, not part of an actuator rod.

DETAILED DESCRIPTION OF THE PREFERRED EMBODIMENTS

In FIG. 1, a load test frame indicated generally at 10 is shown schematically and includes a base 11, and columns 12 that will support an upper crosshead (not shown). A specimen indicated at 13 to be tested is supported between a first specimen grip 14, and a second specimen grip 15 of conventional design, as shown for example in U.S. Pat. No. 3,320,798. The specimen 13 is to be loaded under alternating tension and compression (cyclic) loads. While alternating tension and compression loads are emphasized in this application, it should be noted that many times a "mean" load is provided so that the specimen 13 is always under a tension load but the load is cycled between increasing and decreasing levels, but does not pass through a zero load.

Schematically shown is a loading actuator 20. The actuator is a double acting hydraulic actuator that is normally servovalve controlled and acts through a specimen loading member 21 as shown formed as part of an actuator rod which includes a preloading link mechanism 22 made according to the present invention. The actuator 20 includes an outer housing 23, and an interior piston 24 within the chamber formed by the housing 23. The piston 24 is alternately moved by hydraulic pressure along the longitudinal axis of movement of alternately providing pressure to a pair of chambers 25 and 26 shown above and below the piston in FIG. 2. A servovalve indicated at 27 operates in response to the error signal from combining a preset program signal from a program control 28 and a feedback signal from a feedback transducer 29 (such as for example a load cell in the loading path to the specimen). The program and feedback signals are fed to a summing junction 30 in a normal manner to provide the error signal to the servovalve 27, which selectively provides pressure through lines 32 and 33, respectively, to the chambers 25 and 26.

The piston 24 is connected to loading member 21, which together provide load applying means including an actuator rod 36 which reciprocates along its axis as pressure is alternated between the chambers 25 and 26.

The rod 36 forms a first portion of the loading member 21. A second portion of the loading member comprises the base portion 37 of the grip 15 itself. The base portion transfers load to the internal grip jaws and to the specimen.

A loading link assembly 40 forming part of the link mechanism 22 is connected between the first portion 36 of the loading member and base 37. The first end of the link assembly 40 as shown at 41 is mechanically connected (threaded) to the first loading member portion 36. The link assembly includes a first elongated tubular portion 42 having a neck threaded for the connection 41 and which is positioned in an interior bore 43 of the rod 36. The threaded end has a flange that tightens down on a shoulder formed in first portion 36 as shown at 41A.

In turn, the link assembly 40 includes a second portion comprising a smaller diameter rod 44 on the interior of the first tubular link portion 42. Rod 44 has a first threaded end 45 that threads onto an interior thread of the first tubular link portion 42. The rod 44 extends toward grip 15 along the longitudinal axis of the first portion 36 and has a second end indicated at 50 which is threaded and is adjustably mounted into an interior bore 51 formed in the base portion 37 of the grip 15.

A piston member 52 is fixed to the second link portion 44 (it can be integrally formed) and fits within a bore 53 formed in a housing 54 which also forms a portion of the first loading member. The housing 54 is fixed in place with interfacing shoulder surfaces 55 contiguous. The housing is attached after the threads 41 are tightened and thus permit installing the link. The housing is a part of the first portion 36 of the loading member in the load path from the piston 24 to the grip 15.

A suitable seal 56 is provided around the piston 52, and a second seal 57 is provided around the narrow portion of the rod 44 at a lower end of the chamber 53. A conduit 60 is connected between the seal members and opens into the chamber 53 so that upon supplying fluid under pressure from a suitable valve 61 to the chamber 53 the hydraulic fluid under pressure will tend to urge the piston upwardly, or in direction tending to separate the grip 15 from the first portion 36 of the loading member (which includes housing 54).

The grips are loaded onto the specimen in a normal manner, but in tension-compression loading the connection between the actuator rod or loading member and the grip, generally a threaded stud in conventional systems, will elongate as the specimen is loaded in tension and then shorten again as the specimen is loaded in compression. Unless some load is applied and maintained, as described in U.S. Pat. No. 3,320,798, the backlash in the connection will affect operation of the test machine adversely. Therefore, the present link assembly described is used for preloading and backlash preventing connection between the grip and the actuator piston 24.

As shown in FIG. 3, when hydraulic fluid under pressure is supplied to the chamber 53, the piston 52 is moved upwardly relative to the lower portion of the chamber, and this causes the grip assembly 15, and in particular the base portion 37, to be raised upwardly from first portion 36 of the loading member. A gap is formed as shown at 65, and this causes the rod 44 to be loaded in tension below the piston member 52 and in turn the tube portion 42 of the link assembly is loaded in compression and through the threaded connection 41, the first portion 36 of the loading member is loaded in tension.

With the grip 15 in the position shown in FIG. 3, a shoulder surface 66 on first portion 36 of the loading member faces a mating surface 67 on the underside of the base portion 37 of the grip 15. The hydraulic pressure provided through the conduit 60 is sufficient so that the load on the link assembly 40 is greater than that which is encountered during the actual loading cycle of the specimen 13, and thus the link assembly 40 is preloaded above the normal operating loads. The grip 15 is then merely threaded down onto the threaded end 50 of rod 44 until the surfaces 66 and 67 abut each other. The grip can be tightened by hand, and then the pressure in the chamber 53 is released by operating valve 61. The surfaces 65 and 66 are held together under a preload force from link assembly 40 that is selected to be greater than that encountered during operation.

Because the link 40 is a "folded link" in that the link portions overlap along the axis of the loading member first portion 36. Space is conserved, and the link assembly has an adequate length to provide elongation so that the grip can be tightened to take up the gap after the link assembly is preloaded.

In FIG. 4 a modified form of the invention is shown. In this case, the loading member indicated at 71 comprises a piston rod 72 forming the first portion of the loading member. A piston 70 is mounted on rod 72 and it corresponds to the piston 24 and would be mounted within an outer actuator housing as in the first form of the invention. The rod 72 is the main actuator rod for testing. In this case, the interior of the rod 72 has a bore 73 with a narrowed neck portion 74 that has internal threads.

A loading link 75 comprises a rod link having an end 76 which is threaded into the thread of neck portion 74 on the interior of the rod 72, and which extends along and overlaps the axis of the rod 72. The upper end of the link 75 has a piston 80 formed thereon which fits within a chamber 81 formed directly in the rod 72. This chamber 81 is sealed with suitable seals 82 and 83, respectively so that fluid under pressure can be introduced into chamber 81 through a hydraulic connector 84A that opens to a passageway 84 formed in the piston 80. The fluid under pressure forces the piston 80 upwardly and raises a threaded end 85 of the link 75. The base portion 37 of grip 15 is threaded directly on this threaded end 85, and when the piston member 80 is raised to the level shown by the dotted lines 80A, there will be a space between the rod end surface 86 and the under surface 67 of the grip 15. Again, base 37 of grip 15 forms a second portion of the loading member 71, with rod 72 being the first portion.

Hydraulic pressure supplied through the passageway 84 is sufficient so that the stress in the link 75 is above that which would be encountered during normal loading of the test specimen being held by the grip 15 and loaded through the rod 72. The grip 15 is merely threaded down while maintaining pressure in chamber 81 so that the surface 67 tightly engages the end surface of the first loading portion comprising the rod 72. The second loading portion, which is the base part 37 of the grip 15 is held against the first loading portion under the desired preload that is at a compression level higher than the tension loads encountered during use. In this case, the link that is stressed to clamp the first and second loading members together overlaps the longitudinal axis of the piston rod 72 to save space, and is of a size so that at the desired load level there is a sufficient elongation without overstress of the loading link to permit the first and second loading members to be adjusted to accommodate the preload.

Then, the hydraulic pressure in the chamber 81 is relieved, and the link 75 provides the preload to hold the surfaces 86 and 67 together. The elongation of the loading member is sufficient to maintain the preload after the pressure acting in piston 80 has been released.

In FIG. 5 a further modified form of the invention is shown, and in this form the loading member 91 includes a first portion 92 comprising a piston rod for the testing actuator such as that shown at 72 and 36. Rod 92 also has an interior bore 93. The rod 92 is loaded through a piston in a conventional manner as previously described, and in this form the loading link assembly indicated at 95 includes a first tubular link portion 96 inside the bore 93 that is threaded as at 97 to interior threads in the piston rod 92. A shaft or rod 98 forming a portion of the link assembly 95 extends through the interior of the tubular link portion 96 and is threaded as at 99 to an interior thread in the tubular link portion 96. The shaft or rod 98 has a piston portion 100 at its upper end which is positioned within a piston chamber or cylinder 101 that is formed directly in the end portions of the rod 92, instead of in a separate housing. The tubular link portion 96 has a threaded head member 102 thereon with a flange 103 that seats into a shoulder surface 104 on the interior of the rod 92 when it is threaded fully into place.

The piston portion 100 is sealed with seals 106 and 107, to provide a hydraulic chamber 108 to which hydraulic fluid under pressure can be admitted as shown previously to urge the piston 100 upwardly as shown in FIG. 5, or away from the flange 103. This will create stress in the link portion comprising rod 98 and the tubular link portion 96, carrying load through the threaded connection 97 to the rod 92.

The rod 98 has a threaded end portion 110 that threads into the interior bore 51 of the base portion 37 of a grip 15 as in the previous form of the invention. The base portion 37 comprises a second portion of the loading member 91. The rod 92 of the testing actuator assembly has an end shoulder surface 111 that will abut against the surface 67 of the grip 15. When fluid under pressure is introduced into the chamber 108, the stress level will increase in the link assembly 95 comprising the link rod 98 and the tubular link portion 96 and the grip 15 is raised upwardly as previously explained. The pressure in the chamber 108 will be raised to a level so that the stress in the link assembly 95 exceeds that which is encountered during normal use, and then the grip 15 will be threaded down so that the surface 67 tightly engages the end surface or shoulder surface 111 of the rod 92 to provide a mechanical compressive connection between these two loading member portions. Then the pressure is relieved in the chamber 108 so that the preloading compression force holds the two mating surfaces of the portions of the loading member together under the desired preload to eliminate backlash.

In FIG. 5, it should be noted that a pilot shoulder or boss member 112 is formed as part of the grip member 37, as shown, and this pilot boss forms an annular member that slidably, and closely, fits inside the piston chamber or cylinder 101 so that the grip 37 in this form of the invention is held precisely concentric with the first portion 92 of the loading link (which comprises the piston rod of the testing actuator). In this way, the pilot boss 112 holds the movable portions concentric. The length of the pilot boss 112 is sufficient so that in actual use the amount of elongation of the loading link will not be sufficient so that the pilot moves out of the piston chamber 101. The use of a pilot boss as shown insures that alignment of the parts will be maintained.

The forms of the invention shown in FIGS. 1 through 5 have concentrated on using direct loading members such as piston rods having the loading links with elongated axes overlapping the longitudinal axis of the piston rod. It should be noted that in some cases intermediate pull rods are desirable or necessary, for example in high temperature applications. The loading member could comprises a pull rod, or some intermediate member, which has two portions, with a stressed link between the two portions. The two portions are adjusted after stressing the link so that they mate before the link loading member force is released, to tightly clamp the two loading portions together under the desired preload stress.

The device to preload loading connections can be used where one of the loading members is something other than a piston rod. The arrangement includes a loading member that can be prestressed to the desired level for operation. Referring to FIG. 6, a further modified form of the invention is shown. In this instance, a loading member 120 is positioned between a member which is designed to exert force, and could be, for example, a load cell which is loaded through a hydraulic actuator (not shown). Such a load cell end is shown at 121, and has a threaded opening 122 which is used for connecting a threaded end 123 of a loading link. The threaded end 123 is integral with a piston member 124 which is mounted in an actuator cylinder. The piston in turn is attached to an elongated link 125 that has a threaded end 126 directly connected to a member to be loaded such as a specimen grip or other device 127.

A compression carrying sleeve 130 has an interior passageway 131 that surrounds the link member 125, and is positioned between surfaces of the load cell 121 and the grip 127.

The sleeve 130 has an interior cylinder bore 132 that is of size to receive the piston 124. The piston is sealed relative to the sides of the bore 132 with an O-ring 133. Likewise, the adjacent end of the link 125 is sealed relative to the bore 132 with an O-ring 134. A passageway 135 is provided for introducing fluid under pressure to the underside of the piston 124, which will tend to force the piston toward the load cell 121 with respect to the compression carrying sleeve 130.

The compression carrying sleeve has an end surface 140 that abuts against an end surface 141 of the grip 127, and there is an annular surface 142 on the opposite end of the sleeve 130 surrounding the cylinder bore 132. This surface 142 is adapted to rest or abut against a provided surface 143 of the load cell 121.

When fluid under pressure is introduced into the cylinder bore 132 underneath the piston 124, the piston will be forced in direction toward the load cell, or in other words, in direction as indicated by the arrow 145. This will cause a gap or spacing between the surface 142 and the surface 143, and will stress the link 125 of the loading member and cause it to elongate. The load cell will then be threaded on the end member 123 until the surfaces 142 and 143 again abut (the surfaces 140 and 141 will forced together under the hydraulic pressure on piston 124) and then the pressure will be relieved from the chamber through the passageway 135. The change in length of the rod portion 125 will be sufficient so that even after the surfaces 142 and 143 seat and pressure on piston 124 has been released, the stress level in the link 125 will be sufficiently high so that it will exceed that which is encountered by the loading assembly during the loading of the load cell 121 and the grip 127. It should be understood that a hydraulic actuator would be connected to the load cell for actuating it.

Essentially, this form of the invention is similar to that shown in FIG. 4 except that in place of the actuator rod forming a part of the loading assembly, the sleeve 130 is used and the elongating link can be used to be coupled directly between two members, one of which is a loading member and the other which is the loaded member. The stress level achieved insures that the parts are held properly under alternating tension compression loading.

While hydraulic piston-cylinder assemblies have been shown to be the form for creating the preload stress on the link between the two portions of the loading member, it is to be understood that other types of load applying members, separate from the test load applying member, can be utilized for stressing the link after which adjustment of the two portions of the loading member is made to mechanically load them together under the desired preload.

It should be noted that in all cases, the link that is placed under stress is long enough to produce enough change in length under the hydraulic preloading such that when the hydraulic preloading is removed and the stress loads the mating surfaces tightly together, the change in length (from the maximum length under load to the length of the stressed link when it is in working position) will be sufficient so the preload from the stress in the link will be greater than the maximum load applied during operation of the testing device, or pull rod, or other apparatus using the invention. At the same time, the change in the length of the link must not overstress the link beyond its elastic limit.

What is claimed is:

1. In a device for applying a load to a test specimen, preloading means for providing a mechanical compressive connection between two relatively movable portions of such load applying means at a compression loading greater than any tension loading between the two portions during testing of a specimen, including load applying means adapted to be coupled from a loading actuator to a specimen and having first and second portions, an elastic link having one end coupled to a first portion of the load applying means, and the other end coupled to the second portion of the load applying means, means carried by the load applying means and acting between the first and second portions to selectively stress said elastic link to a first stress level greater than the stress occurring in said elastic link between the first and second portions when the load applying means has reached its maximum load, the first and second portions separating when the means to stress the elastic link is at the first stress level, means to engage said first and second portions and adapted to carry compression loads between the first and second portions when the means to selectively stress the elastic link is at the first stress level, the means to selectively stress being thereafter releasable whereby the stress in the elastic link loads the second portion mechanically against the first portion.

2. The apparatus of claim 1 wherein said load applying means comprises a load applying rod forming the first portion, said rod having a longitudinal axis and the second portion of the load applying means being at one end of the rod, said link having a longitudinal axis that overlaps the longitudinal axis of said first portion.

3. The apparatus of claim 1 wherein said means to stress the link comprises a hydraulic cylinder and piston assembly, and means to apply fluid pressure to said cylinder and piston assembly to stress said link to tend to space the first and second portions; and said means to engage comprises means to permit the second portion to be mechanically moved into contact with the first portion, said first and second portions being held together under a preload force from the elastic link when the means to stress has been released.

4. The device of claim 1 wherein the first and second portions of said load applying means comprise generally coaxial members, said coaxial members having sections with facing shoulder surfaces, and the means to engage comprises said facing shoulder surfaces which will abut when the first and second portions are engaged.

5. The device as specified in claim 1 wherein said elastic link comprises a rod member, said rod member being connected at one end to said first portion of the load applying means and at the other end to the second portion of the load applying means, said first and second portions of said load applying means having shoulder surfaces that comprise the means for engaging the first and second portions.

6. The device of claim 1 wherein said independent means to stress comprises a hydraulic cylinder assembly which will load the elastic link when the hydraulic cylinder assembly is subjected to hydraulic pressure.

7. The apparatus as specified in claim 6 wherein said hydraulic cylinder assembly comprises the first portion of the load applying means, said first portion comprising a piston rod having a central bore, and said link is mounted substantially within said bore.

8. A test specimen loading device including a grip member, a hydraulic actuator having a rod, means to connect said grip member to said rod comprising a link having a longitudinal axis that overlaps the longitudinal axis of said rod, one end portion of said link being mechanically connected to said rod, and the other end portion of said link being mechanically connected to said grip member, means carried by the rod to permit selectively stressing said link under a load tending to separate the grip member and said rod, said means to permit stressing said link stressing the link to a higher stress level than that encountered during normal operation of said test specimen loading device, and means to permit supporting an end of the rod relative to said grip member to carry compression loads when said means to permit stressing is stressing the link while said grip member remains connected to its associated end of said link, the means to permit stressing being releasable after the grip is supported on said rod so that the stress in said link loads the means to permit supporting the grip member and rod together under a desired compressive preload.

9. The device of claim 8 wherein said link comprises two link portions, a first link portion being tubular and connected to said rod at one end, said first portion extending from its connection to the rod away from the grip to a remote end, a second link portion being positioned within the first tubular link portion and connected to the tubular link portion at the remote end thereof and extending toward and being connected to said grip.

10. The device of claim 9 wherein the rod has a central chamber defined therein, the majority of the link being positioned in the central chamber.

11. In a device for applying a load to a test specimen, preloading means for providing a mechanical compressive connection between two relatively movable portions of such load applying means at a compression loading greater than any tension loading between the two portions during testing of a specimen, including a rod having a first end connected to an actuator piston and a second end, said rod comprising a first portion of the load applying means and having an interior bore open at the second end thereof and extending generally along the longitudinal axis thereof, an elastic link mounted in said bore, said elastic link comprising first and second link portions, a first link portion being tubular and being connected to said rod and extending within said bore in direction away from the second end of the rod, a second link portion being mounted within the interior of the tubular first link portion and having an inner end connected to said first link portion at an end of the first link portion spaced from the second end of the rod, said second link portion having an outer end extending outwardly beyond the second end of said rod and having means for connecting a second portion of the load applying means to the outer end of the second link portion, means acting between the rod and the second link portion to selectively stress the first and second link portions to a first stress level greater than the stress occurring in said elastic link when the load applying means has reached its normal load during testing of a specimen, the outer end of the second link portion moving in direction away from the second end of the rod when the means to stress are operated to stress the elastic link, and means to provide a compression carrying connection between the rod and a second portion of the load applying means when such second portion is connected to the outer end of the second link portion, the means to stress being releasable with the second portion of the load applying means connected to the second link portion and the means to provide a compression carrying connection in place, whereby the stress in the elastic link loads the second portion of the load applying means connected to the second link portion in compression against the rod.

12. The apparatus of claim 11 wherein said means acting between the rod and the second link portion to selectively stress the first and second link portions comprises a hydraulic actuator including a piston mounted on the second link portion adjacent the second end of said rod, the bore in said rod having a portion forming a hydraulic cylinder to receive the piston portion, and means to fluidly seal the first and second link portions relative to each other and relative to the rod to form a hydraulic chamber which when subjected to pressure will tend to force the outer end of the second link portion in a direction away from the second end of the rod.

13. The apparatus as specified in claim 12 wherein the means for connecting a second portion of the load applying means to the second link portion comprises a threaded end at the outer end of said second link portion, and the means to provide a compression carrying connection comprises an end surface of the rod which is substantially perpendicular to the longitudinal axis of the rod and is in position to be abutted against the second portion of the load applying means threadably mounted on the threaded end of said second link portion.

14. In a test specimen loading device for connection to a grip assembly for loading a specimen from a hydraulic actuator having an actuator rod, the improvement comprising a rod for the hydraulic actuator, means to connect a specimen grip assembly to said rod comprising an elastic link having a longitudinal axis that overlaps the longitudinal axis of said rod, one end portion of said link being mechanically connected to said rod and the other end portion of said link having threadable means for threadably connecting the link to a grip assembly, means carried by the rod for selectively stressing said link under a load tending to separate a grip assembly connected to the link and said rod, said means for stressing said link being operable to stress the link to a higher stress level than that encountered during normal operation of such test specimen loading device, the threadable means permitting threading a grip assembly on the threadable means when said means to permit stressing is stressing the link to a position with the end of the rod abutting such grip assembly while such grip assembly remains connected to said link, the means to permit stressing being releasable after such grip assembly is in abutting relationship with said rod so that the stress in said link loads such abutting surfaces together under a desired compressive preload.

* * * * *

UNITED STATES PATENT AND TRADEMARK OFFICE
CERTIFICATE OF CORRECTION

PATENT NO. : 4,475,403
DATED : October 9, 1984
INVENTOR(S) : Thomas P. Lentz

It is certified that error appears in the above-identified patent and that said Letters Patent is hereby corrected as shown below:

Column 8, line 5, (Claim 6, line 1), after "said" remove --independent--.

Signed and Sealed this

Twelfth Day of March 1985

[SEAL]

Attest:

DONALD J. QUIGG

Attesting Officer    Acting Commissioner of Patents and Trademarks